(12) United States Patent
Zhang

(10) Patent No.: US 6,215,554 B1
(45) Date of Patent: Apr. 10, 2001

(54) LASER DIAGNOSTIC UNIT FOR DETECTING CARCINOSIS

(76) Inventor: Yi Zhang, 35 Shi Wei Road, He Ping District, Shenyang, 110014 (CN)

( * ) Notice: Subject to any disclaimer, the term of this patent is extended or adjusted under 35 U.S.C. 154(b) by 0 days.

(21) Appl. No.: 09/383,660

(22) Filed: Aug. 26, 1999

(51) Int. Cl.$^7$ ............................ G01N 33/48; G01N 21/47
(52) U.S. Cl. .............................................. 356/446; 356/39
(58) Field of Search ..................... 356/446, 447, 356/448, 300, 301, 303, 306, 317, 318, 326, 331, 332, 333, 39, 40

(56) References Cited

U.S. PATENT DOCUMENTS

| | | | |
|---|---|---|---|
| 4,832,483 | * 5/1989 | Verma | 356/39 |
| 5,072,338 | * 12/1991 | Hug et al. | 362/32 |
| 5,786,893 | * 7/1998 | Fink et al. | 356/301 |
| 6,002,476 | * 12/1999 | Treado | 356/301 |

* cited by examiner

*Primary Examiner*—Frank G. Font
*Assistant Examiner*—Michael P. Stafira
(74) *Attorney, Agent, or Firm*—Michael I. Kroll

(57) ABSTRACT

A laser diagnostic unit for detection of carcinosis and method of detecting carcinosis in a patient by examining a specimen taken from the patient. The laser diagnostic unit includes a specimen well for retaining the specimen therein and a laser for irradiating the specimen within the specimen well. A monochromator having an entrance slit receives light scattered by the specimen within the specimen well through the slit and a photomultiplier for converting light dispersed in said monochromator into electrical signals. The electrical signals are provided to a microprocessor for analyzing the signals and generate a spectrogram of the laser light irradiating the specimen. The spectrogram will indicate that the specimen is cancerous upon detection of differences with a spectrogram created by irradiation of a non-cancerous specimen. The laser used to irradiate the specimen is preferably an argon laser and a power source is connected to the argon laser and is able to regulate a current supplied to the argon laser, thereby regulating the wavelength of the light beam produced by the argon laser.

5 Claims, 15 Drawing Sheets

A. Fluorescence spectrum under 514.5nm. excitation before interacting time span

B. Raman spectrum under 514.5nm. excitation before interacting time span

C. Fluorecence spectrum under 488.0nm. excitation

D. Raman spectrum under 486.0nm. excitation before interacting time span

F. Raman spectrum under 514.5 nm. excitation after interacting time span

E. Fluorescence spectrum under 514.5 nm. excitation after interacting time span locality of peak (nm) 585

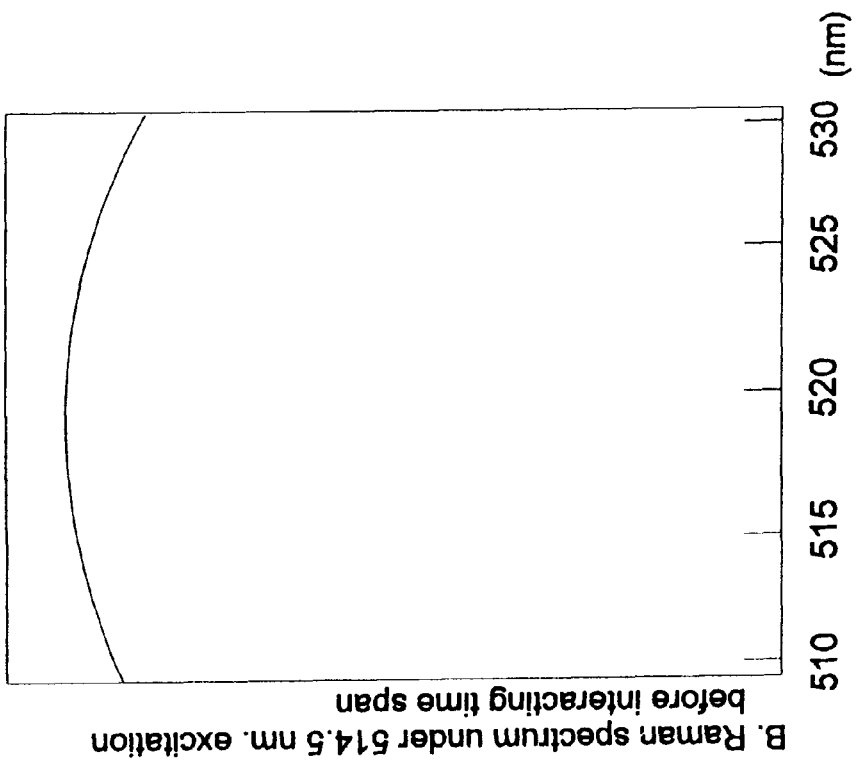
B. Raman spectrum under 514.5 nm. excitation before interacting time span
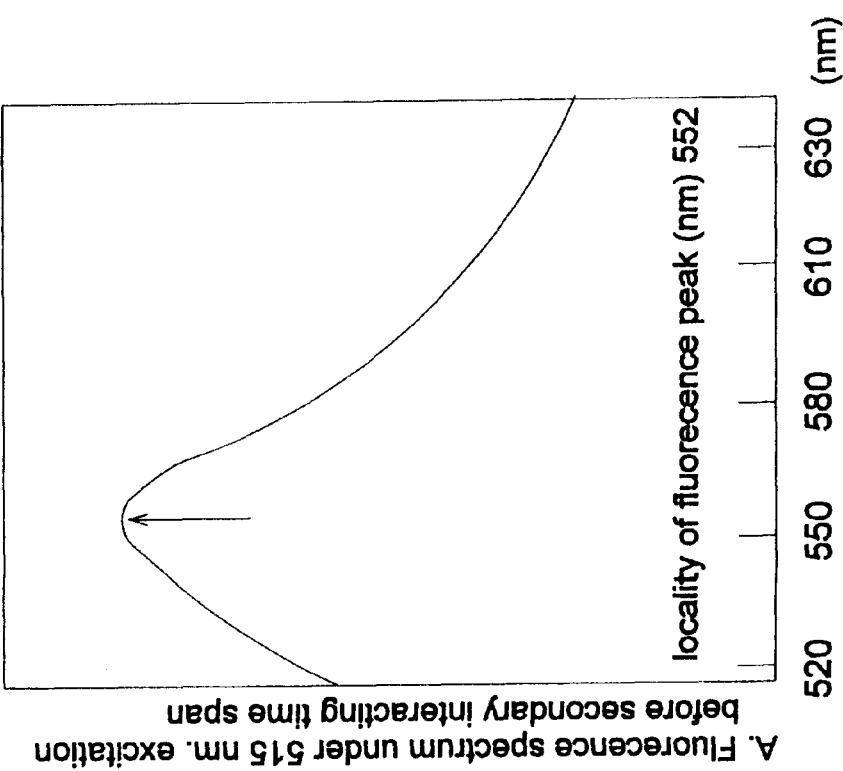
A. Fluorecence spectrum under 515 nm. excitation before secondary interacting time span
locality of fluorecence peak (nm) 552
FIG 5B
FIG 5A

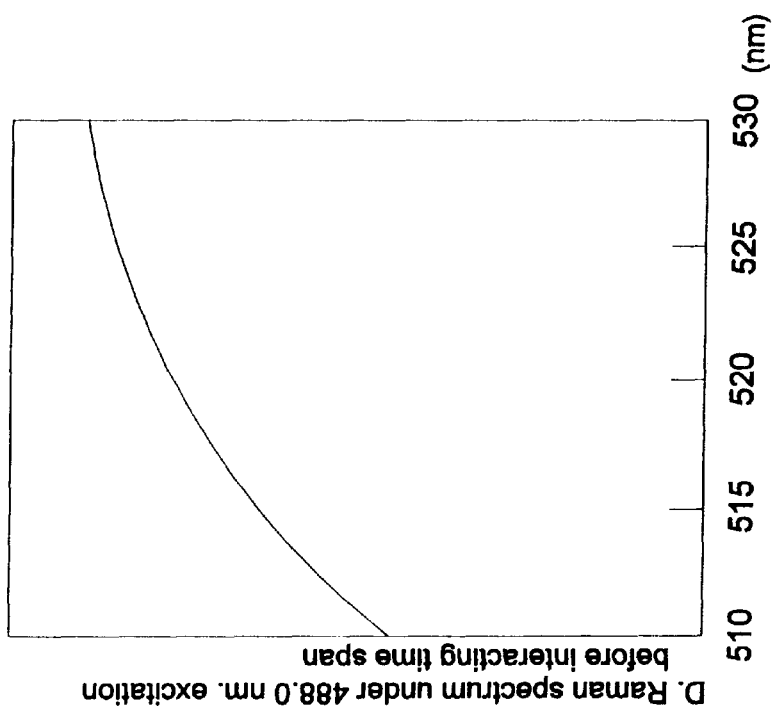
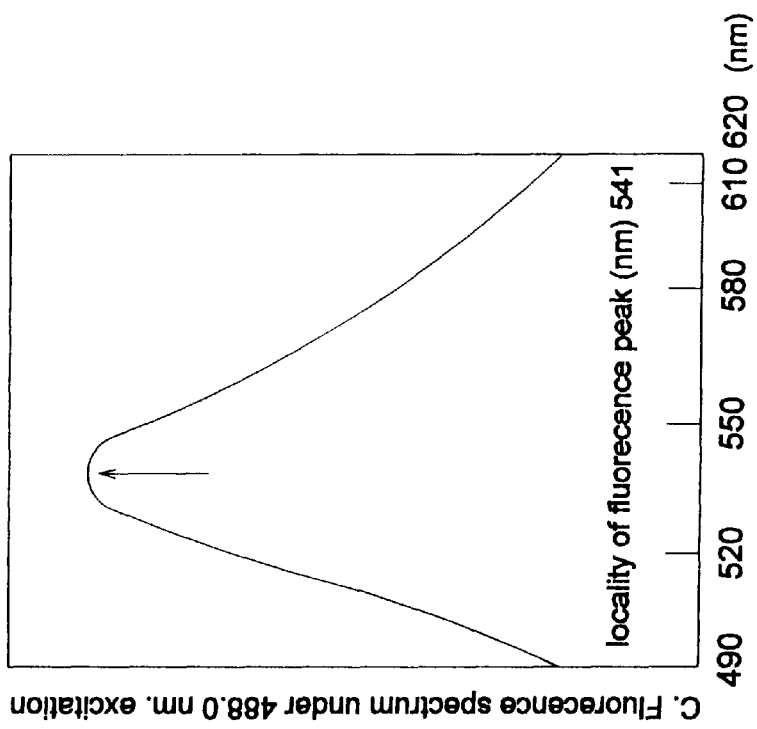
FIG 5D
FIG 5C

F. Raman spectrum under 514.5 nm. excitation after interacting time span

E. Fluorecence spectrum under 514.5 nm. after interacting time span locality of fluorecence peak (nm) 562

B. Raman spectrum under 514.5 nm. excitation after interacting time span

A. Fluorescence spectrum under 514.5 nm. before interacting time span

D. Raman spectrum under 488.0 nm. excitation before interacting time span

C. Fluorescence spectrum under 488.0 nm.

locality of fluorecence peak (nm) 537

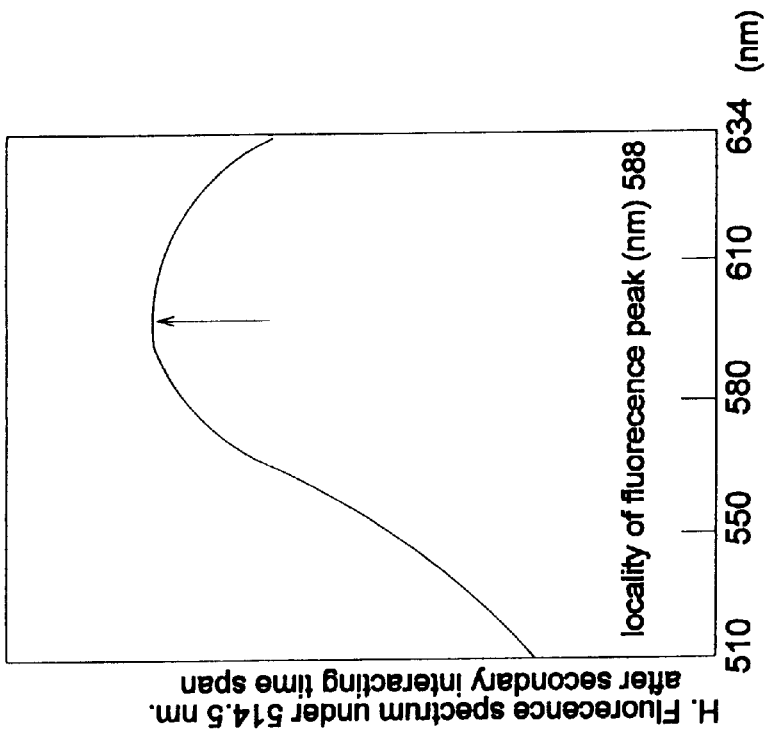
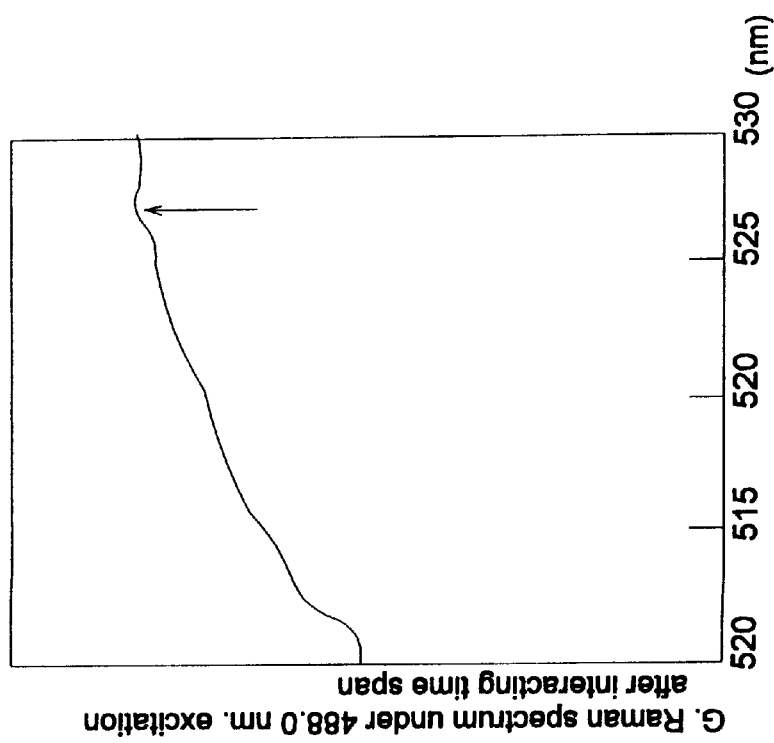

LASER DIAGNOSTIC UNIT FOR DETECTING CARCINOSIS

BACKGROUND OF THE INVENTION

1. Field of the Invention

The present invention relates generally to devices for detecting cancerous cells and, more specifically, to a laser device for checking for the existence of carcinosis based upon an analysis of the laser spectrum of a specimen taken from a patient.

2. Description of the Prior Art

Carcinosis is a disease having a high mortality rate posing a great threat to humankind. This disease is one of the three leading causes of death. Due to these factors, detecting the existence of carcinogenic cells in the body is of great importance. The earlier the cells are detected, the greater the chance of treating the disease effectively. In order to provide an effective measure for detecting carcinosis in the body, numerous different devices have been utilized over the years to check for the existence of carcinosis. Such devices have generally centered around imaging techniques such as CT, β ultrasonic, X-ray, NMR and endoscope. The final diagnosis being dependent on the pathological findings. However, these devices were difficult to operate, were not sensitive enough to obtain an accurate reading and also provided difficulty in obtaining a diagnosis. The devices also subject the patient to atrogenic damage and were unable to detect precancerous cells at a molecular level thus making it difficult to detect a carcinoma at an early stage. While these units may be suitable for the particular purpose to which they address, they would not be as suitable for the purposes of the present invention as heretofore described.

It is thus desirable to provide a laser diagnostic unit for detection of carcinosis which is able to detect and diagnose carcinosis at a molecular level therefore allowing for detecting of precancerous changes at an early stage. It is further desirable to provide a laser diagnostic unit for detection of carcinosis which is easy to use and provides a rapid diagnosis. It is still further desirable to provide a laser diagnostic unit for detection of carcinosis which will not cause iatrogenic damage to a patient.

SUMMARY OF THE PRESENT INVENTION

The present invention relates generally to devices for detecting cancerous cells and, more specifically, to a laser device for checking for the existence of carcinosis based upon an analysis of the laser spectrum of a specimen taken from a patient.

A primary object of the present invention is to provide a laser diagnostic unit for detection of carcinosis that will overcome the shortcomings of prior art devices.

Another object of the present invention is to provide a laser diagnostic unit for detection of carcinosis which is able to detect carcinosis on a molecular level to thereby detect precancerous changes at an early stage.

A further object of the present invention is to provide a laser diagnostic unit for detection of carcinosis including an argon laser for checking for the existence of carcinosis.

A yet further object of the present invention is to provide a laser diagnostic unit for detection of carcinosis wherein the laser spectrum created by irradiating a sample taken from a patient with a light beam produced by the argon laser is analyzed to detect irregularities from a spectrum produced by normal non-cancerous samples to thereby determine the existence of carcinosis.

A still further object of the present invention is to provide a laser diagnostic unit for detection of carcinosis which does not produce side effects, iatrogenic damage and pain for a patient being tested.

An even further object of the present invention is to provide a laser diagnostic unit for detection of carcinosis which requires only 0.5 m/l of serum/blood sample for purposes of diagnosis wherein no special treatment of the serum is needed, thus, mass surveys of patients may be easily and readily obtained.

A yet further object of the present invention is to provide a laser diagnostic unit for detection of carcinosis which is capable of examining any type of tumor on any part of the body thereby allowing use of the device during regular health check-ups to screen out carcinosis patients.

A yet further object of the present invention is to provide a laser diagnostic unit for detection of carcinosis able to provide a printout of diagnosis results automatically immediately after examination.

A still further object of the present invention is to provide a laser diagnostic unit for detection of carcinosis able to differentiate between benign and malignant tumors and provide dynamic monitoring of patients in post-operation convalescence stays and during regular checks of cancer patients during treatment.

Another object of the present invention is to provide a laser diagnostic unit for detection of carcinosis that is simple and easy to use.

A still further object of the present invention is to provide a laser diagnostic unit for detection of carcinosis that is economical in cost to manufacture.

Additional objects of the present invention will appear as the description proceeds.

A laser diagnostic unit for detection of carcinosis and method of detecting carcinosis in a patient by examining a specimen taken from the patient is disclosed by the present invention. The laser diagnostic unit includes a specimen well for retaining the specimen therein and a laser for irradiating the specimen within the specimen well. A monochromator having an entrance slit receives light scattered by the specimen within the specimen well through the slit and a photomultiplier for converting light dispersed in said monochromator into electrical signals. The electrical signals are provided to a microprocessor for analyzing the signals and generate a spectrogram of the laser light irradiating the specimen. The spectrogram will indicate that the specimen is cancerous upon detection of differences with a spectrogram created by irradiation of a non-cancerous specimen. The laser used to irradiate the specimen is preferably an argon laser and a power source is connected to the argon laser and is able to regulate a current supplied to the argon laser, thereby regulating the wavelength of the light beam produced by the argon laser.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects features and attendant advantages of the present invention will become more fully appreciated as the same becomes better understood when considered in conjunction with the accompanying drawings, in which like reference characters designate the same or similar parts throughout the several views.

FIGS. 5A–5H are graphs of Serous spectrograms of patients with pancreatic carcinoma; and FIGS. 6A–6H are graphs of Serous spectrograms of patients with pulmonary carcinoma.

DESCRIPTION OF THE REFERENCED NUMERALS

Figure 1:
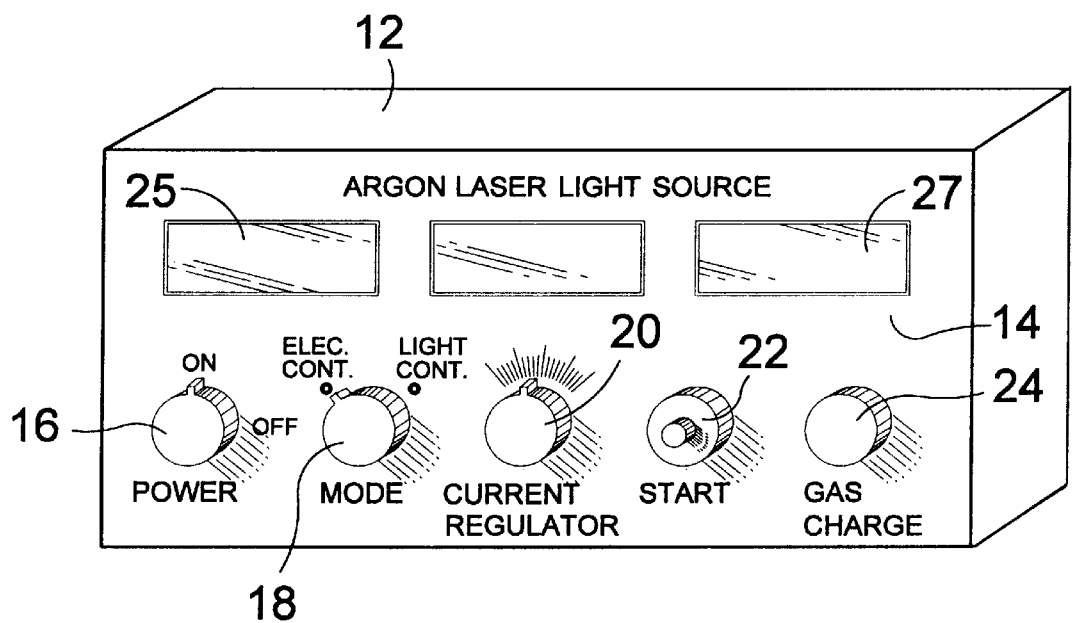
FIG. 1 is a front perspective view of a laser diagnostic unit for detection of carcinosis of the present invention.

Turning now descriptively to the drawings, in which similar reference characters denote similar elements throughout the several views, the Figures illustrate the laser diagnostic unit for detection of carcinosis of the present invention. With regard to the reference numerals used, the following numbering is used throughout the various drawing figures.

- 10 a laser diagnostic unit for detection of carcinosis of the present invention
- 12 housing of the laser diagnostic unit
- 14 face side of the housing of the laser diagnostic unit
- 16 power switch on face side of the housing of the laser diagnostic unit
- 18 mode switch on face side of the housing of the laser diagnostic unit
- 20 current regulating switch on face side of the housing of the laser diagnostic unit
- 22 start switch on face side of the housing of the laser diagnostic unit
- 24 gas charge switch on face side of the housing of the laser diagnostic unit
- 25 display for ammeter
- 26 double grating monochromator
- 27 display for volt meter
- 28 specimen well
- 30 relective surface
- 32 Argon laser
- 34 power supply
- 36 PMT
- 38 pre amplifier
- 40 A/D converter
- 42 microprocessor
- 44 drive device
- 46 output device
- 48 high voltage power supply
- 50 chopper
- 52 sample
- 54 lens
- 56 lock in amplifier

DETAILED DESCRIPTION OF THE PREFERRED EMBODIMENT

Figure 2:
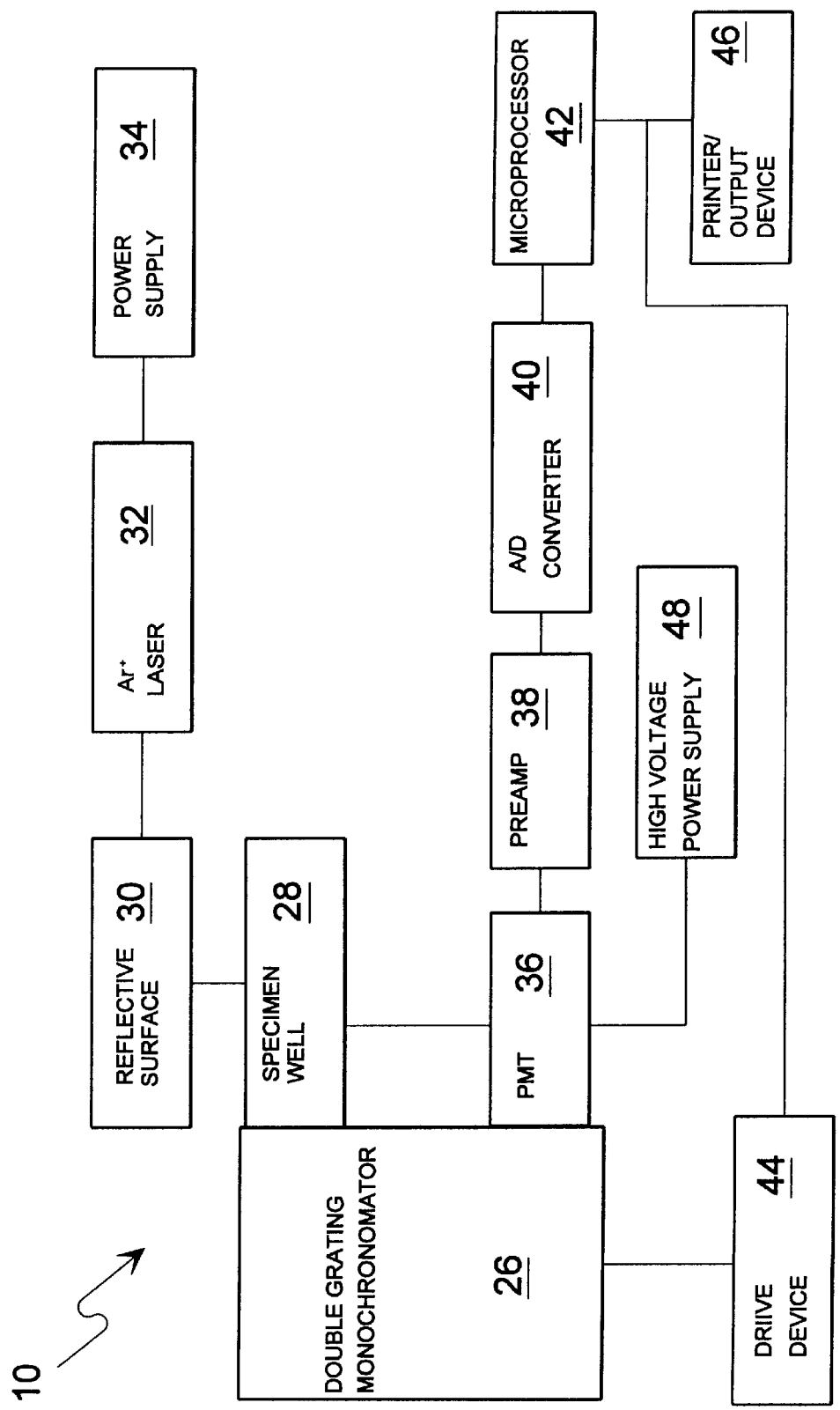
FIG. 2 is a block diagram of the laser diagnostic unit for detection of carcinosis of the present invention.
Figure 3:
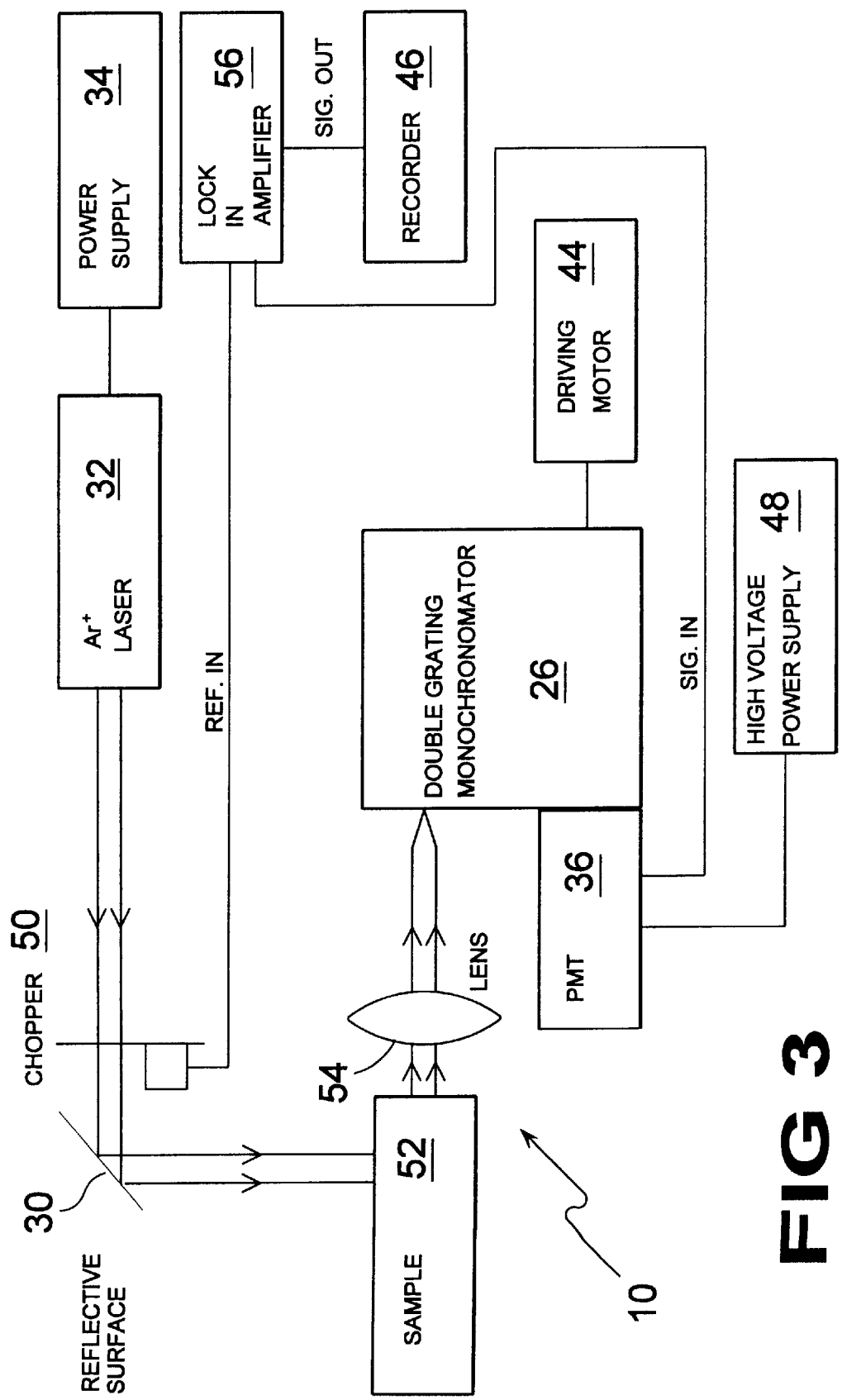
FIG. 3 is a block diagram of tile laser diagnostic unit for detection of carcinosis of the present invention using a Serous Flourescence-Raman Spectrum Diagnosis.
Figure 4A:
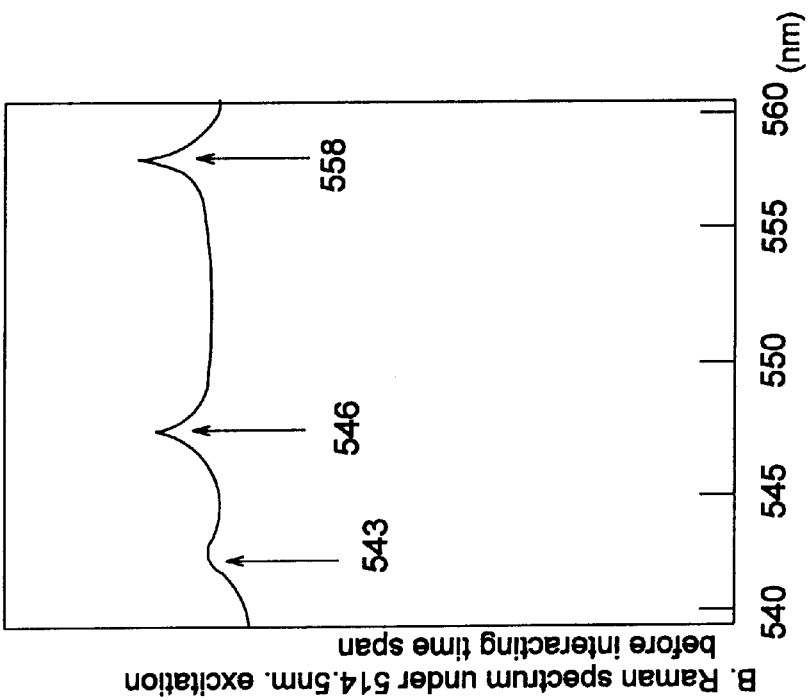
FIGS. 4A–4H are graphs of Serous spectrograms of normal human serum.
Figure 4B:
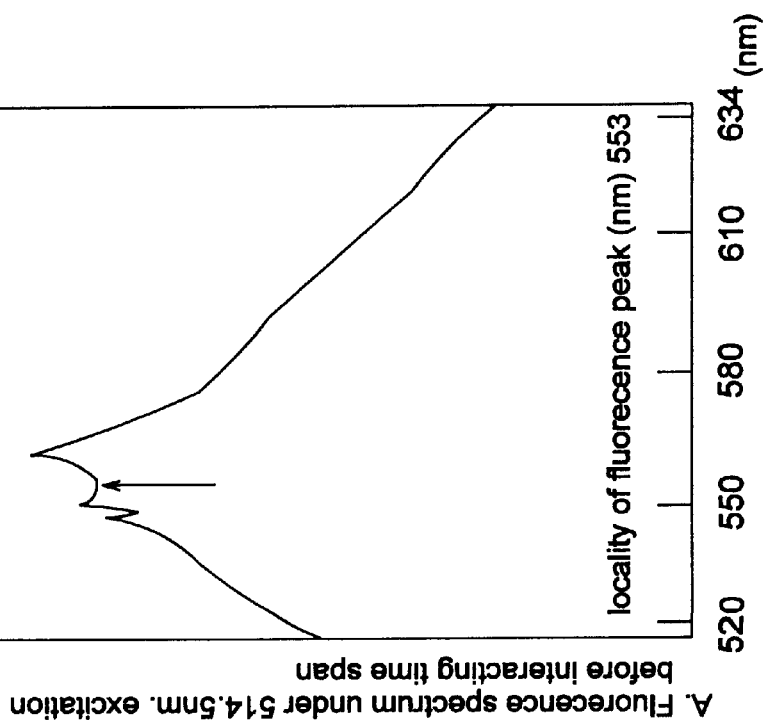
Figure 4C:
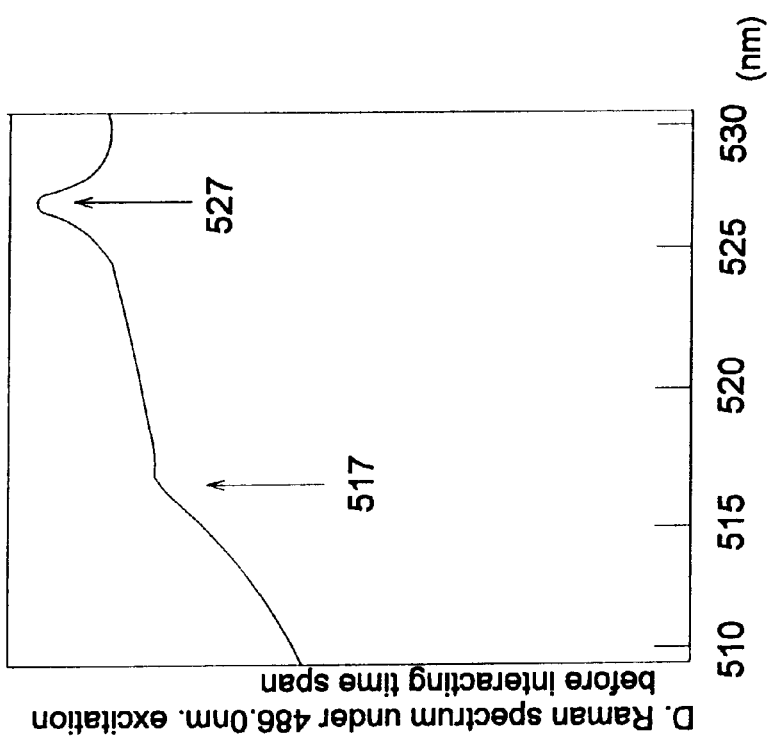
Figure 4D:
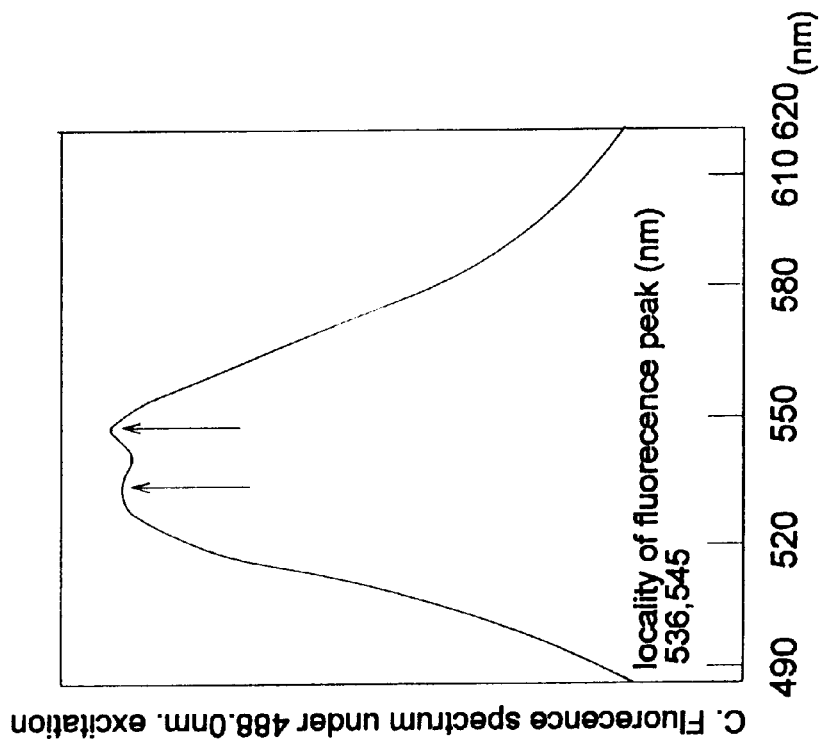
Figure 4F:
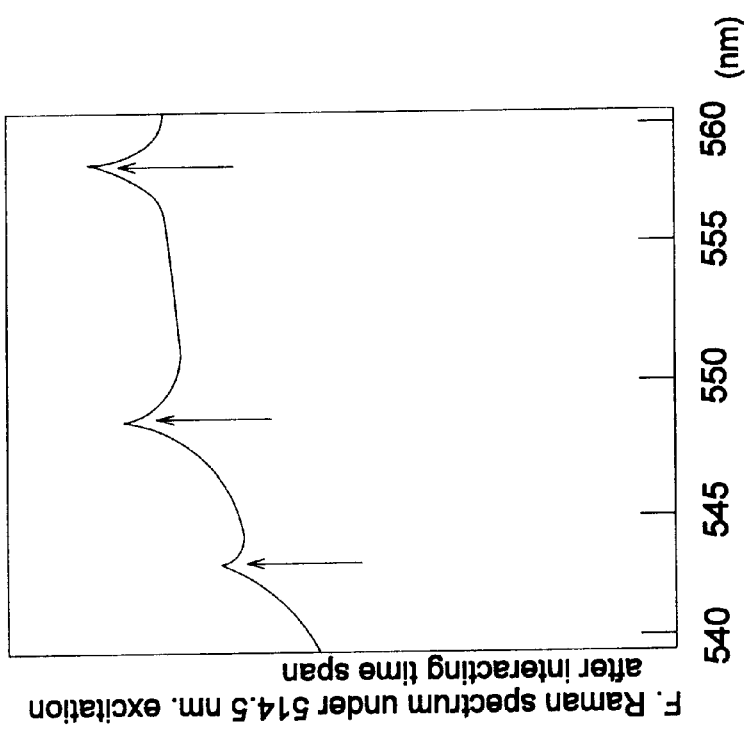
Figure 4E:
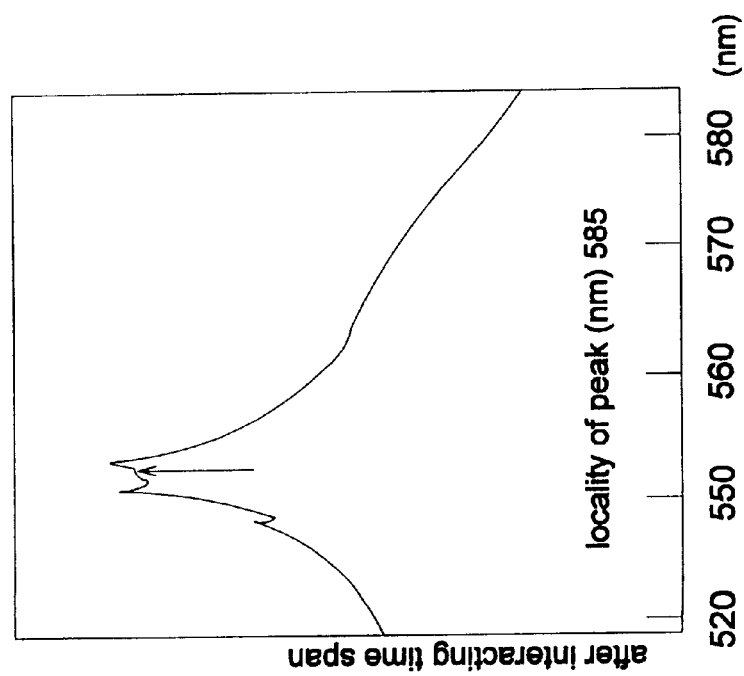
Figure 4H:
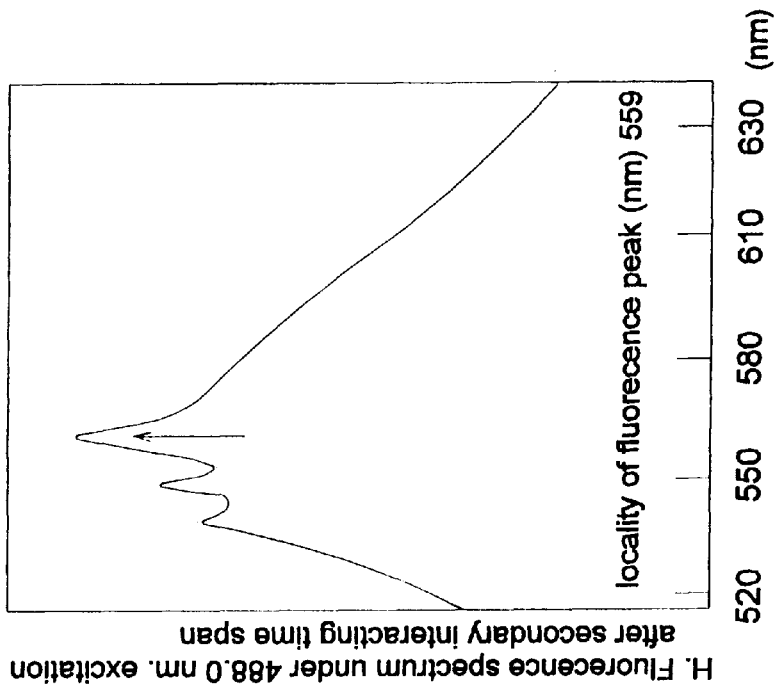
Figure 4G:
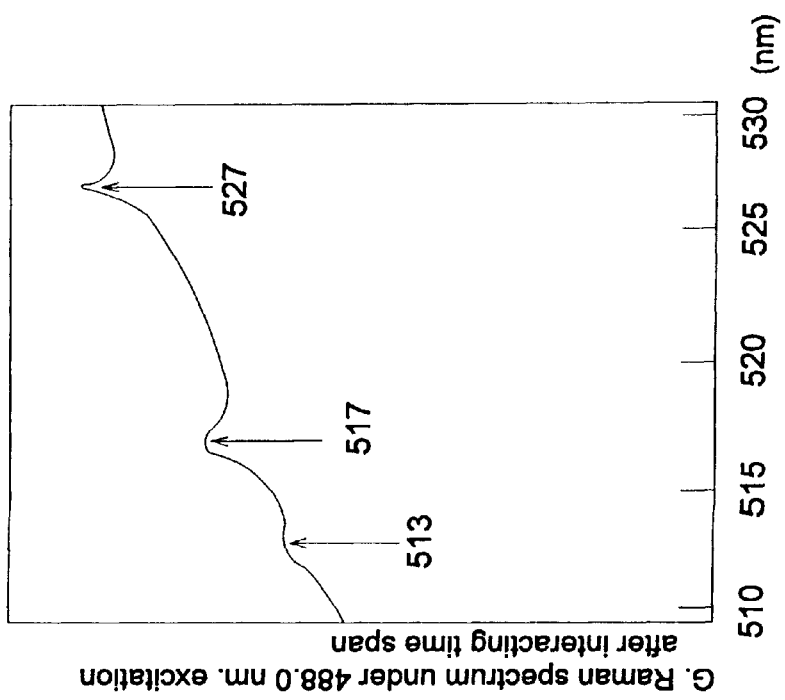
Figure 5F:
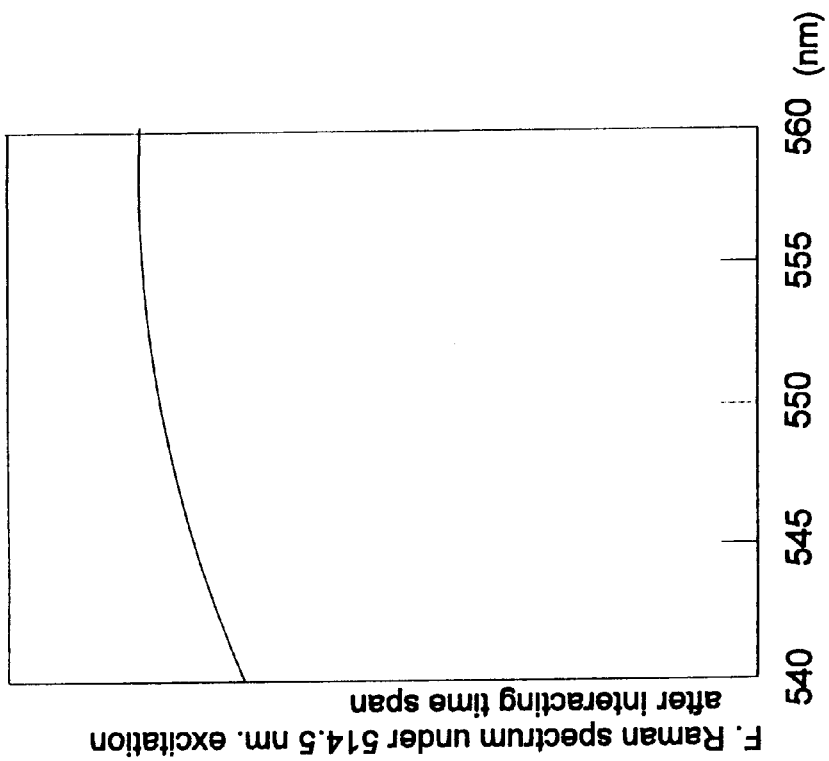
Figure 5E:
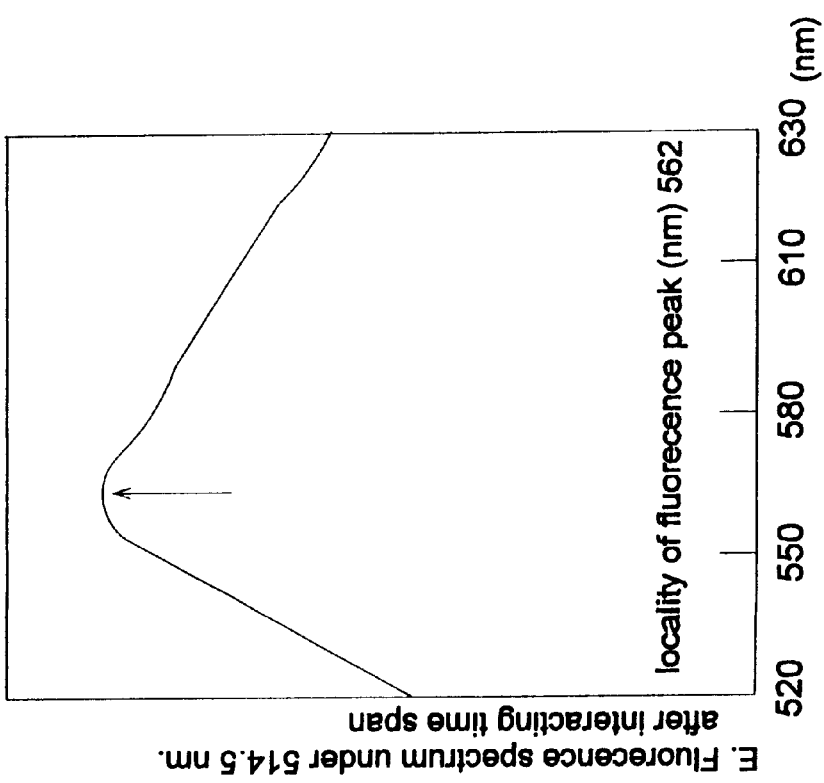
Figure 5H:
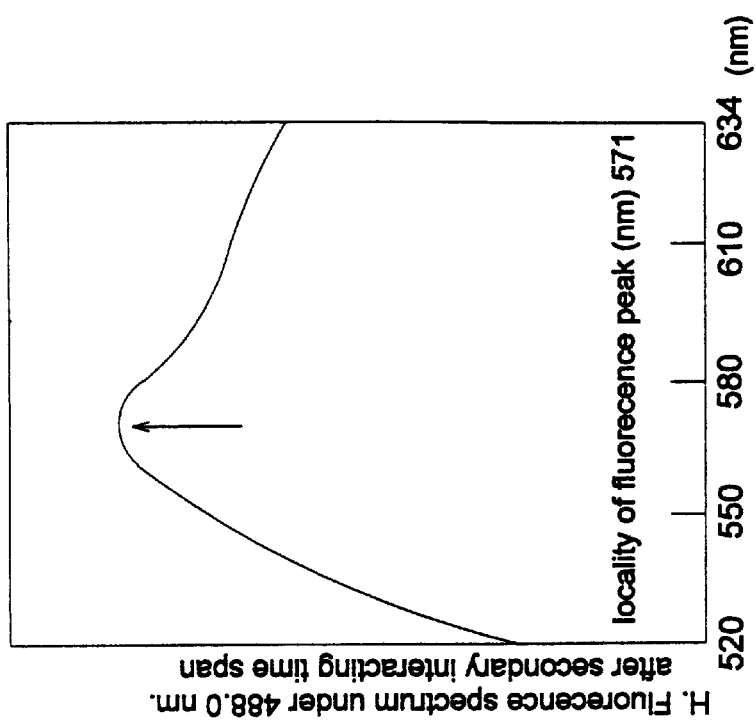
Figure 5G:
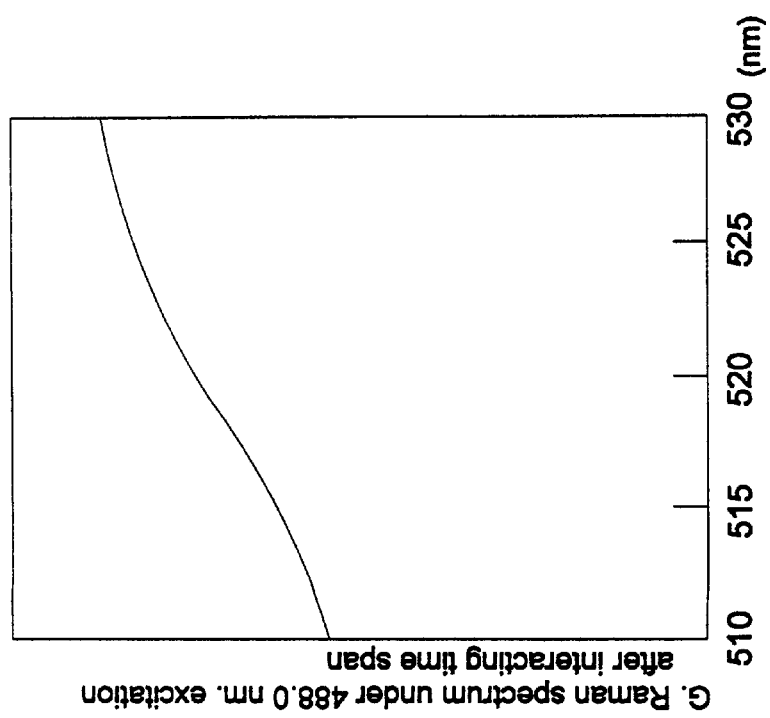
Figure 6B:
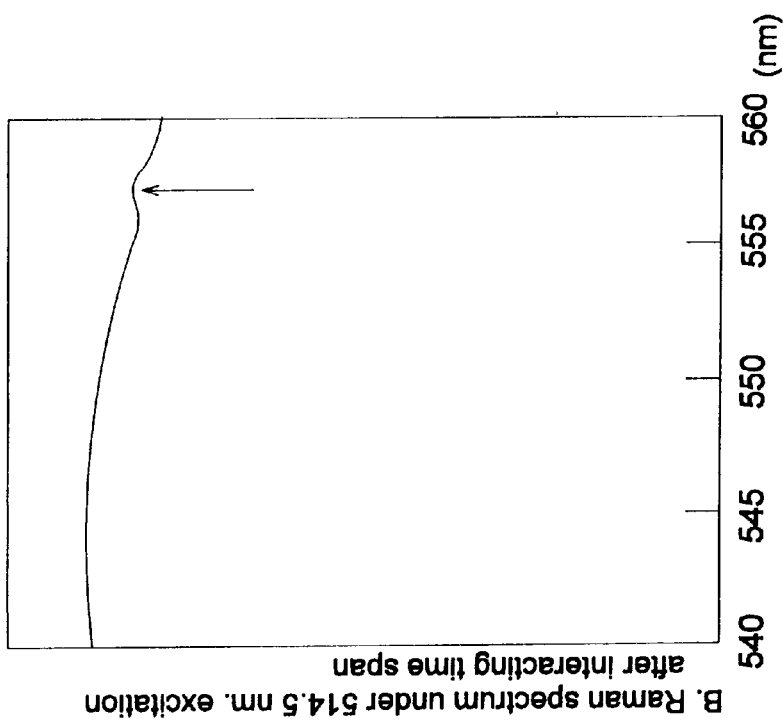
Figure 6A:
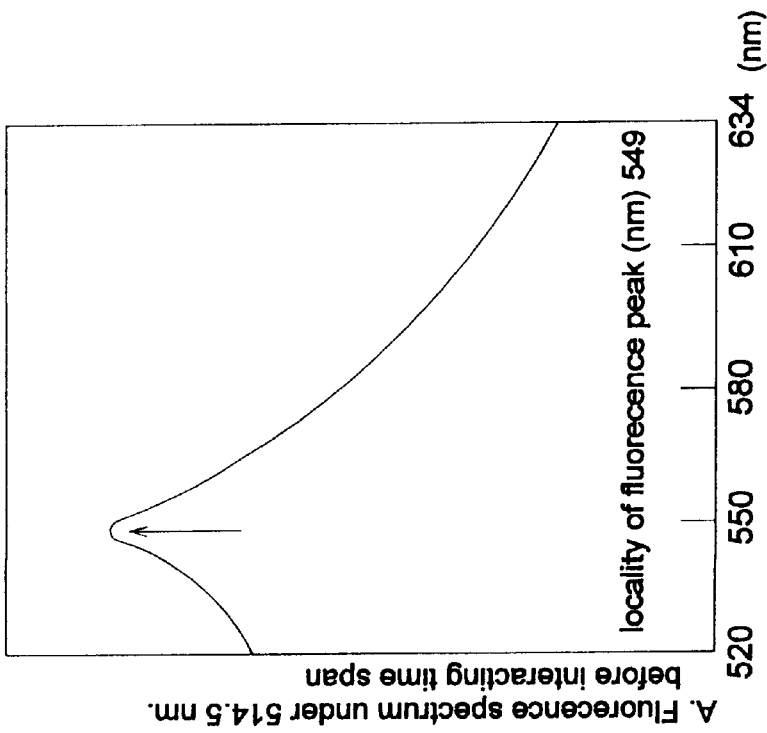
Figure 6D:
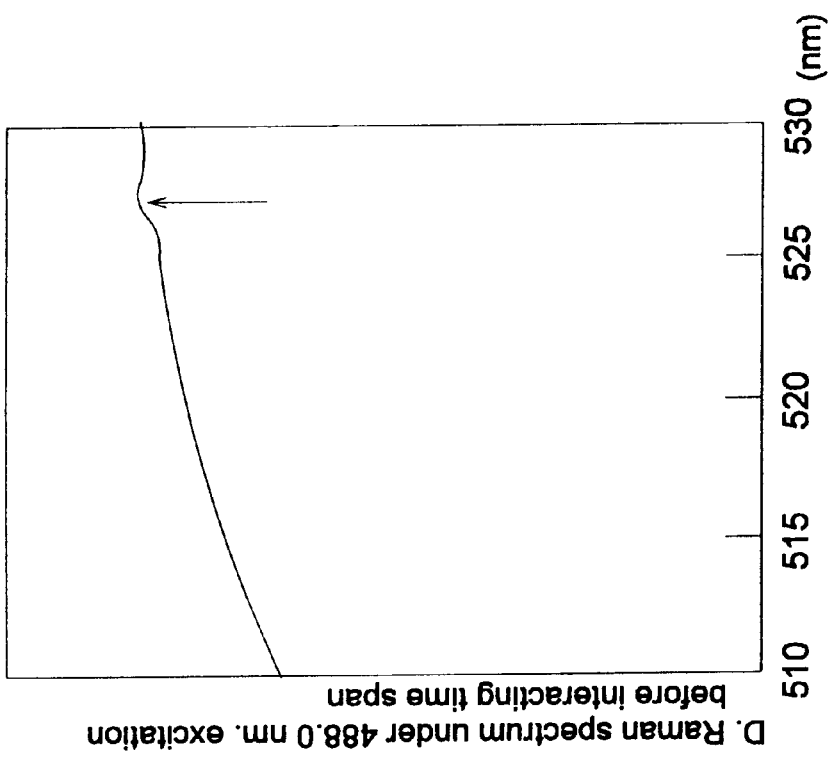
Figure 6C:
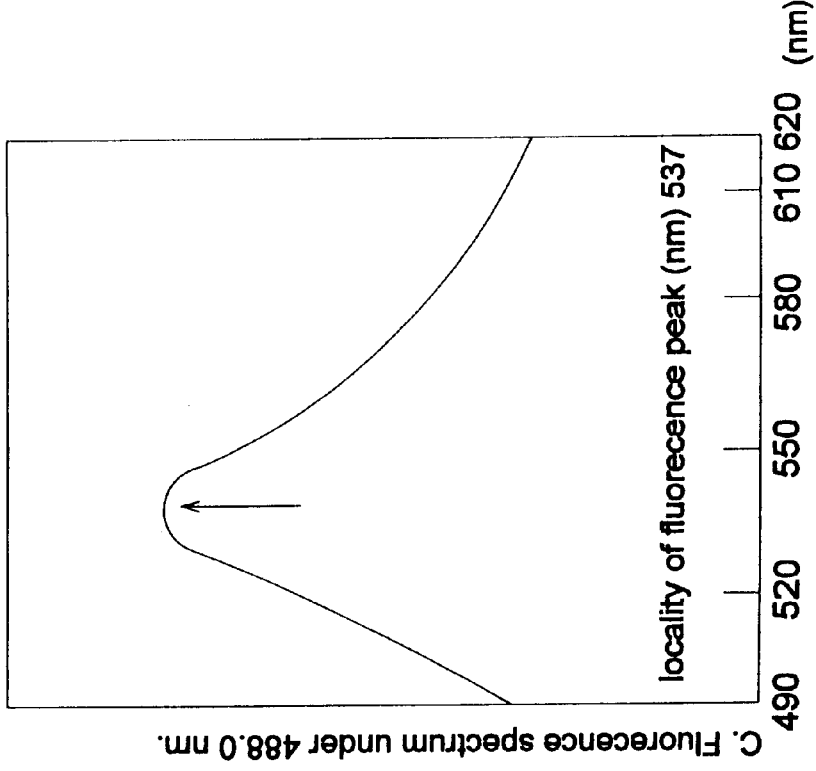
Figure 6E:
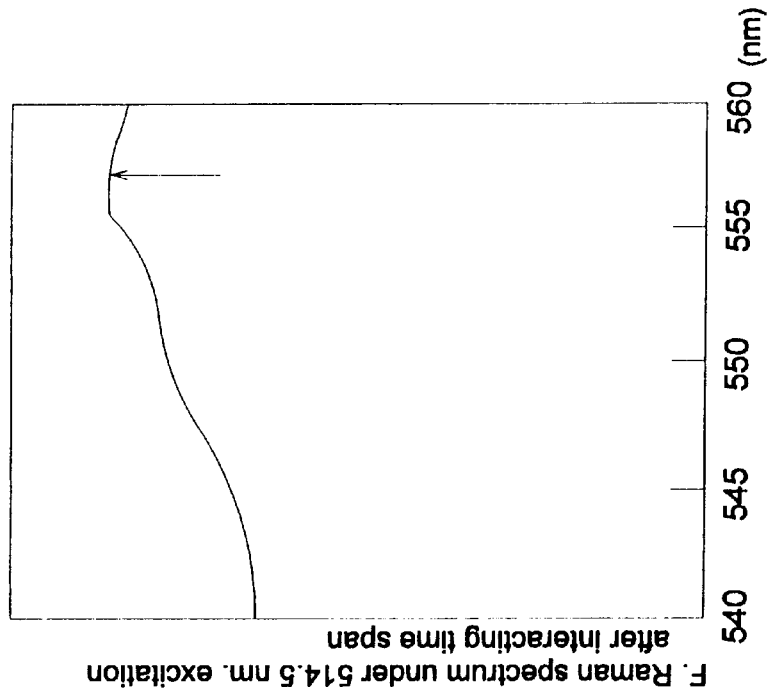
Figure 6F:
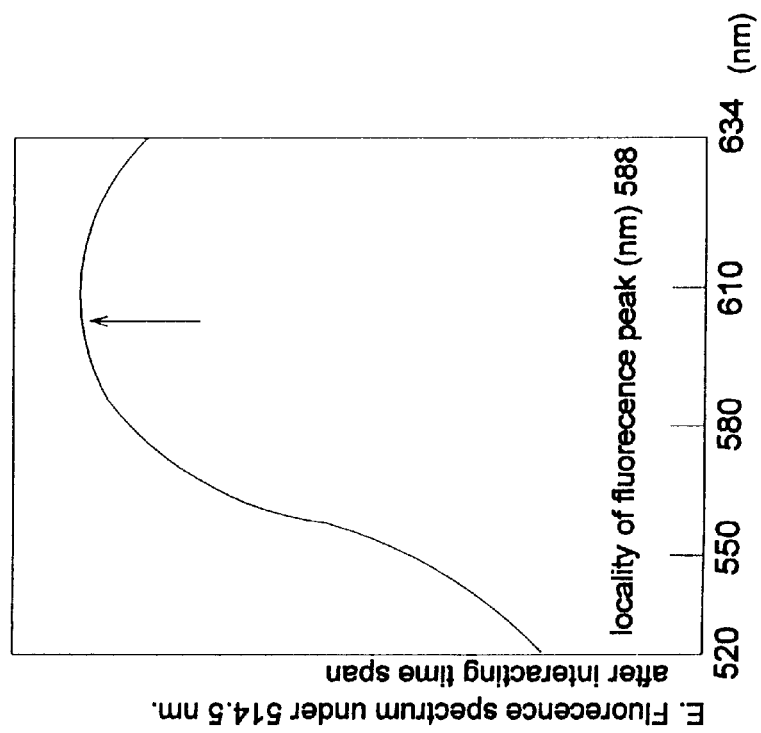

Turning now descriptively to the drawings, in which similar reference characters denote similar elements throughout the several views, FIGS. 1 through 3 illustrate the laser diagnostic unit for detection of carcinosis of the present invention indicated generally by the numeral 10.

The laser diagnostic unit 10 is used for checking for and detecting carcinosis. This device operates based upon laser spectrum analysis by detecting differences in the molecular spectra of serum which exist between cancerous and non-cancerous patients. The diagnostic results are obtained through the detection of Serous fluorescence and Raman spectra obtained using an argon (Ar+) laser according to certain scientific criteria. By detecting the distinct differences which exist in the molecular structure of serum obtained from a patient having cancer as opposed to a patient who is free of cancer, cancer may be discovered at the molecular level thus allowing detection and diagnosis of precancerous changes and early stages of carcinoma early in their formation.

A perspective view of the power supply 12 for the argon laser used in the laser diagnostic unit 10 is illustrated in FIG. 1. The power supply 12 includes a face side 14 on which a plurality of control knobs are positioned. A first control knob 16 turns on the power supply 12 to provide power to the argon laser. A second control knob 18 sets the mode of operation of the power source 12. The mode control knob 18 sets the power source to operate in either an electrical control mode or a light control mode. A third control knob 20 regulates the current supplied to the argon laser and thus determines the strength of the light beam produced by the laser. A fourth control knob 22 starts the supply of power to the argon laser. A fifth control knob 24 provides a charge to the argon gas used by the argon laser, i.e. excites the argon gas. An ammeter is provided within the power source for measuring the current and providing a readout of the measured current on the display 25. A voltmeter is also provided with a display 27 for displaying the rectified voltage supplied by the power source 12.

A block diagram showing the laser diagnostic unit 10 of the present invention is illustrated in FIG. 2. The laser diagnostic unit 10 consists of a laser 32 which receives power from the power supply 34, a specimen well 28, a double grating monochromator 26 and a microprocessor 42. The serum to be examined for the existence of precancerous and cancerous cells is placed in the specimen well. The serum is preferably a blood sample taken from the patient and requires no special treatment or preparation prior to analysis by the laser diagnostic unit 10. Normally, only approximately 0.5 ml of serum is needed for the diagnosis.

When power is supplied to the argon laser 32 from the power source 34, the light from the laser 32 reflects off a reflective surface 30 positioned in front of the laser 32 and is directed to irradiate the serum within the specimen well 28. Preferably a Model A-237 Ar+ laser having a maximum output of 4 w is used as the light source. Light beams of 5145 Å, 4580 Å, 4765 Å, etc. are used for purposes of diagnosis. The light is excited by the serum to produce excited fluorescence and Raman scattering light which enters the double grating monochromator 26 through a slit therein. After chromatic dispersion fluorescence within the double grating monochromator 26 the scattered light is converted into an electrical signal by a photomultiplier 36 and amplified by a preamplifier 38. The amplified electrical signal is converted to a digital signal by an A/D converter 40 and provided to the microprocessor 42. The microprocessor 42 will process the received digital signal to generate a diagnostic result. The diagnostic result generated by the microprocessor 42 is then provided to a printer or alternative output device 46 for analysis by a physician. A drive device 44 is connected to both the monochromator 26 and the microprocessor 42 for inputting data thereto for use in the processing of the signal. Such data to be input includes data representative of a normal non-cancerous serum spectrums, patient identification data, patient history and other pertinent information A high voltage power supply 48 is provided to drive the photomultiplier 36.

In designing the system two main points must be considered. These points are to collect as much fluorescence as possible and to match with the entrance aperture of the double grating monochromator. Furthermore, it is desired to make the system as small as possible.

An alternative set up for the laser diagnostic unit 10 is illustrated in FIG. 3. The argon laser illustrated in this figure is designed to provide a 488.0 nm and 514 nm laser beam for irradiating the sample 52 through the dioptic system. The power supply 34 supplies power to the laser 32 causing the generation of the laser beam. The laser beam passes through a chopper 50 for filtering the laser beam prior to reaching the reflective surface 30. The chopper has a modulated frequency of 700 Hz. and generates a reference signal in response to receipt of the laser beam thereby. The reference signal is provided to a lock in amplifier 56. The reflected signal is directed to irradiate the sample 52. The fluorescence-Raman signals produced upon irradiation of the sample 52 are directed towards a lens 54. The lens 54 focuses the fluorescence-Raman signals for direction through an entrance slit in the double grating monochromator 26. At an output slit of the double grating monochromator 26 is a photomultiplier 36. The output of the photomultiplier 36 is provided to the lock in amplifier 56 and the output signal from the lock in amplifier is provided to and recorded by an XY recorder 46. The data recorded on the XY recorder 46 can then be analyzed by a physician to determine whether the sample is cancerous.

FIGS. 4, 5 and 6 illustrate Serous spectrograms generated using the laser diagnostic unit 10 from samples taken from healthy patients, patients with pancreas carcinoma and patients with pulmonary carcinoma, respectively. FIGS. 4A, 5A and 6A are fluorescence spectrums under 514.5 nm excitation before certain time spans of interactions between laser light and the serum. FIGS. 4B, 5B and 6B are Raman spectrums under 514.5 nm excitation before certain time spans of interactions between laser light and the serum. FIGS. 4C, 5C and 6C are fluorescence spectrums under 488.0 nm excitation before certain time spans of interactions between laser light and the serum. FIGS. 4D, 5D and 6D ) are Raman spectrums under 488.0 nm excitation before certain time spans of interactions between laser light and the serum. FIGS. 4E, 5E and 6E are fluorescence spectrums under 514.5 nm excitation after certain time spans of interactions between laser light and the serum. FIGS. 4F, 5F and 6F are Raman spectrums under 514.5 nm excitation after certain time spans of interactions between laser light and the serum. FIGS. 4G, 5G and 6G are fluorescence spectrums under 488.0 nm excitation after certain time spans of interactions between laser light and the serum. FIGS. 4H, 5H and 6H are fluorescence spectrums under 488.0 nm excitation after secondary interacting time spans.

Through comparisons of these graphs certain findings have been made. Such findings include that in the spectra produced from normal human serum, there appear to be three Raman peaks at Raman shifts of 1010 cm$^{-1}$, 1160 cm$^{-1}$ and 1525 cm$^{-1}$, respectively for 514.5 nm excitations and also three Raman peaks at the same Raman shifts for 488.0 nm excitations. For example, the relative intensity of the Raman peak at the shift 1525 cm$^{-1}$ are greater for 514.5 nm Raman peaks than for 488.0 nm Raman peaks. For normal human serum a last Raman peak always exists while for cancerous serum, there exists no Raman peak in some occasions or the relative intensities of the Raman peak excited by 514.5 nm laser beams are weaker than those for Raman peaks excited by 488.0 nm laser beams.

From the A's and E's of FIGS. 4, 5 and 6 we are able to see some red shifts of fluorescence peaks to different degrees after the time spans of laser light acting on the serum. For normal, non-cancerous samples the amounts of red shifts are generally less than those for patients with carcinoma in the Serous spectra.

From the E's and H's of FIGS. 4, 5 and 6 we can see that the fluorescence intensities at 600 nm~640 nm are slightly stronger with respect to 520 nm. However, the intensified amounts are smaller for healthy non-cancerous samples than for patients with carcinoma in their serum.

Due to noises which always appear with high frequency fluctuations and "burrs" on the spectral curves a smoothing technique is often used to obtain a clear form of spectrogram for analysis. The laser diagnostic unit 10 uses a method of accumulation and averaging combined with a least square smoothing technique to smooth the obtained spectrogram. The smoothing of the spectrogram helps to eliminate the effects of noise on the spectrogram and therefore allow a more accurate and easily analyzed spectrogram.

The operation of the laser diagnostic unit for detection of carcinosis 10 will now be described with reference to the figures. In operation, the laser diagnostic unit for detection of carcinosis 10 is first assembled by connecting cooling water tubing to the power supply and laser whereby a water flow rate shall not be below 20 liters/minute. The cooling water tubing and water running therethrough will help to cool the power supply and laser to avoid overheating and damage to the power supply and laser. The power switch 14 of the power supply 12 is then activated. At this point the gas pressure of the argon laser must be checked to insure that the pressure is less than 20 $\mu$Å. If the pressure is greater than 20 $\mu$Å gas leakage may result. When the power button 14 is activated, the cathode of the laser begins to heat and the Ammeter on the power supply indicates the current of the magnetic field. The rectified voltage provided by the power supply 12 is displayed by the display 27 for the voltmeter. The rectified voltage should be 20–40 volts higher than the voltage drop of the left laser working voltage.

After preheating for 30 minutes, the laser is ready to be triggered. At this time the displays for the ammeter and volt meter should read 0. The mode knob of the power supply is now switched to electrical control mode. The current regulation knob 20 is turned clockwise to set the laser to a working current of 30 Å. Pressing of the start button 22 at this time causes the laser to enter the working state wherein the desired working current value may be set. The voltage drop of the laser must be regulated to be within the range of 20–40 volts and use of a voltage over 50 volts is forbidden. The laser diagnostic unit 10 is now set into operation.

The user will now turn on the controller of the stepping motor and negative high-voltage power supply and then turn on the microprocessor 42. The laser must be regulated to give an output of 514.5 nm singlet laser light and the current regulation knob 20 is adjusted to provide an output power of 280 mW. The serum is know placed into the specimen well 28 and left there without being irradiated.

Once the microprocessor begins operation, the operation program is preferably operating using the windows operating system, the screen of the microprocessor will display the title "Laser Auto-Fluorescence-Raman Spectrum Diagnosis for Carcinomas" and displays the following selections in a first option screen:

|  |  |  |  | P = 0.280 | W |
|---|---|---|---|---|---|
| Case History | C | Collecting | M | Y = 0.000 | V |
| Processing | P | Diagnosis | D | Display | S |
| Setting | Y | Help | H | Printing | R |

Using the mouse to select the option for inputting "case history" the screen will now display to following:

| New Case History | N |
|---|---|
| Open Case History | O |
| Case History record | Q |
| Case History write | W |
| Exit | Alt + F4 |

When entering a new case history, the file name shall not exceed 8 characters. The screen should then be returned to the first option screen.

The incidence slit of the double grating monochromator is then adjusted to a smaller size and the laser is allowed to irradiate the specimen. At this time the user will select the displayed option for "collecting" and the following display screen will be displayed:

| Setting of Spectrum | E |
|---|---|
| Setting of Collecting | S |
| Peak Value Testing | P |
| Zero point Testing | Z |
| Start Collecting | I |

Upon selecting setting of Spectrum, the display will show the following options to be selected from.

| 5145 | Fluorescent Spectrum |
|---|---|
| 5145 | Raman Spectrum |
| 4880 | Fluorescent Spectrum |
| 4880 | Raman Spectrum |

The user will select the 5145 Fluorescent Spectrum option, input the appropriate gains and cause the display of the first option screen to read y=4.000 v. When this procedure is complete, the first option screen will be displayed. If the value of y is not 4.000 v then the slit width of the double grating monochromator must be further adjusted.

The "collecting" option is next selected by the user and the following will be displayed on the display of the microprocessor:

| Setting of Spectrum | E |
|---|---|
| Setting of Collecting | S |
| Peak Value Testing | P |
| Zero point Testing | Z |
| Start Collecting | I | and the monochromator will begin to scan the 5145 fluorescent spectrum. When the 5145 fluorescent scanning ends, the laser light is blocked. The laser is now regulated to provide an output of 488.0 nm singlet laser light. The current regulation knob is also adjusted to provide an output power of 310 m W. This procedure is repeated for the 5145 fluorescence detection.

After irradiation of the specimen, the width of the slit of the double grating monochromator is regulated such that the value of Y is approximately 4,000 volts. The 4880 fluorescent spectrum scanning will now be performed beginning from the irradiation and timing steps.

After the specimen has been irradiated for 8 minutes with a laser having a wavelength of 488.0 nm the same regulating and operating procedures as performed for the 5145 fluorescence detection is performed as discussed above. After resetting the monochromator back to 560 nm the 5145 fluorescence is again detected. The 4880 Raman spectrum will next be detected using the above described procedure and the 5145 fluorescence spectrum will be detected once again. When the output waveform is regulated it is important that the laser light be blocked and not allowed to irradiate the specimen directly.

All detections of spectrum are now complete and the microprocessor will now process all the data to provide a diagnosis. The results of the diagnosis may then be displayed or printed out on an output device such as a printer or monitor. If additional specimens are to be examined, the above procedures are repeated for the new specimen. If all specimens have been examined, the unit is shut off by first exiting the software program and then turning off the stepping motor controller and high-voltage power supply. The power button on the power source is then activated to turn the power source off and thereby shut down the laser. The laser and cooling water supply may be turned off about 10 minutes later.

Certain precautions should be taken when using the laser diagnostic unit 10 of the present invention. Firstly, the water tubing should be shut off immediately if the water supply is stopped during operation. The laser may then be restarted 30 minutes later. Secondly, direct exposure of the laser light to the eyes of a user should be avoided and the platform on which the laser and monochromator are placed shall be stable. Thirdly, the incidence angle of the slit and the optical paths shall not be randomly changed. Finally, the specimen to be examined shall not be stained with red color after being processed and shall be stored in a refrigerator at 4° C. and maintained free from pollution and freezing.

From the above description it can be seen that the laser diagnostic unit for detection of carcinosis of the present invention is able to overcome the shortcomings of prior art devices by providing a laser diagnostic unit which is able to detect carcinosis on a molecular level to thereby detect precancerous changes at an early stage. The laser diagnostic unit includes an argon laser for use in checking for the existence of carcinosis wherein the laser spectrum of the argon laser is analyzed to determine the existence of carcinosis. The laser diagnostic unit produces no side effects, iatrogenic damage and pain and requires only 0.5 ml of serum for purposes of diagnosis wherein no special treatment of the serum is needed, thus, mass surveys of patients may be easily and readily obtained. The laser diagnostic unit is capable of examining any type of tumor on any part of the body thereby allowing use of the device during regular health check-ups to screen out carcinosis patients and provides a printout of diagnosis results automatically immediately after examination. The laser diagnostic unit is also able to differentiate between benign and malignant tumors and provide dynamic monitoring of patients in post-operation convalescence stays and during regular checks of cancer patients during treatment. Furthermore, the laser diagnostic unit of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A method of detecting in a mass survey of patients the presence of carcinosis in specimens comprising the steps of:
    a) for each patient placing a specimen of only about 0.5 ml of not specially treated serum/blood in a specimen well;
    b) irradiating said specimen in the specimen well with a light beam from an argon laser at a regulated wave length in the range of 488.0 to 514.5 nm to thereby scatter the light beam;
    c) collecting the scattered light beam in a monochromator;
    d) generating from said scattered light a digital data signal from the collected scattered light;
    e) generating a spectrogram of the scattered light beam from the data signal; and
    f) comparing the generated spectrogram to a spectrogram from a specimen not containing cancerous cells to determine whether said specimen contains cancerous cells and the type of said cancerous cells to screen out carcinosis patients and provide a printout of diagnosis results for each patient immediately after examination.

2. The method of claim 1, wherein the monochromator collects the scattered light through a slit in one side thereof.

3. The method of claim 1, further comprising the step of reflecting the light beam by a reflective surface to irradiate the specimen within the specimen well.

4. The method of claim 1, further comprising the step of recording the spectrogram created by the microprocessor.

5. The method of claim 4, wherein said step of recording is performed by a printer connected to the microprocessor and the spectrogram is recorded on paper.

* * * * *